(12) United States Patent
Scirica et al.

(10) Patent No.: US 10,426,480 B2
(45) Date of Patent: Oct. 1, 2019

(54) CUTTING RING ASSEMBLY WITH RIGID CUTTING MEMBER

(71) Applicant: Covidien LP, Mansfield, MA (US)

(72) Inventors: Paul A. Scirica, Huntington, CT (US); Steven Joyce, Wallingford, CT (US); Justin Williams, Southbury, CT (US); Charles Kollar, Fairfield, CT (US); Christopher Penna, Guilford, CT (US)

(73) Assignee: Covidien LP, Mansfield, MA (US)

( * ) Notice: Subject to any disclaimer, the term of this patent is extended or adjusted under 35 U.S.C. 154(b) by 589 days.

(21) Appl. No.: 15/072,420

(22) Filed: Mar. 17, 2016

(65) Prior Publication Data

US 2016/0317152 A1 Nov. 3, 2016

Related U.S. Application Data

(60) Provisional application No. 62/154,213, filed on Apr. 29, 2015.

(51) Int. Cl.
| | | |
|---|---|---|
| *A61B 17/115* | (2006.01) | |
| *A61B 17/10* | (2006.01) | |
| *A61B 17/11* | (2006.01) | |
| *A61B 17/068* | (2006.01) | |
| *A61B 17/072* | (2006.01) | |

(52) U.S. Cl.
CPC .......... *A61B 17/105* (2013.01); *A61B 17/068* (2013.01); *A61B 17/1114* (2013.01); *A61B 17/1155* (2013.01); *A61B 2017/07257* (2013.01); *A61B 2017/07285* (2013.01)

(58) Field of Classification Search
CPC .......... A61B 17/32053; A61B 17/1155; A61B 17/115; A61B 17/1114

USPC ............................................ 227/176.1, 180.1
See application file for complete search history.

(56) References Cited

U.S. PATENT DOCUMENTS

| | | | |
|---|---|---|---|
| 3,193,165 | A | 7/1965 | Akhalaya et al. |
| 3,388,847 | A | 6/1968 | Kasulin et al. |
| 3,552,626 | A | 1/1971 | Astafiev et al. |
| 3,638,652 | A | 2/1972 | Kelley |
| 3,771,526 | A | 11/1973 | Rudie |

(Continued)

FOREIGN PATENT DOCUMENTS

| | | |
|---|---|---|
| CA | 908529 A | 8/1972 |
| CA | 2553139 A1 | 2/1996 |

(Continued)

OTHER PUBLICATIONS

Extended European Search Report for EP 16 16 7444 dated Aug. 30, 2016.

(Continued)

*Primary Examiner* — Andrew M Tecco
*Assistant Examiner* — Eyamindae C Jallow

(57) ABSTRACT

The present disclosure relates to a cut ring assembly including a backup member, an intermediate member and a cutting ring body. The intermediate member is formed of a thin, rigid material that is sandwiched between the backup member and the cutting ring body. The thin, rigid material is formed of a material having a hardness less than the hardness of the backup member and greater than the hardness of the cutting ring body. The present disclosure also relates to an anvil assembly including such a cut ring assembly.

20 Claims, 5 Drawing Sheets

(56) References Cited

U.S. PATENT DOCUMENTS

| | | |
|---|---|---|
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |

(56) References Cited

U.S. PATENT DOCUMENTS

| | | |
|---|---|---|
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Willman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |

(56) References Cited

U.S. PATENT DOCUMENTS

| | | |
|---|---|---|
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 2003/0111507 A1 | 6/2003 | Nunez |
| 2005/0051597 A1 | 3/2005 | Toledano |
| 2005/0107813 A1 | 5/2005 | Gilete Garcia |
| 2005/0205639 A1 | 9/2005 | Milliman |
| 2005/0205640 A1* | 9/2005 | Milliman .......... A61B 17/1155 227/176.1 |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0038401 A1* | 2/2010 | Milliman .......... A61B 17/1114 227/175.1 |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |

(56) References Cited

U.S. PATENT DOCUMENTS

| | | |
|---|---|---|
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0367450 A1* | 12/2014 | Williams ............ A61B 17/115 227/181.1 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2153781 A2 | 2/2010 |
| EP | 2215977 A2 | 8/2010 |
| EP | 2524656 A2 | 11/2012 |
| EP | 2524658 A1 | 11/2012 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 2001/054594 A1 | 8/2001 |
| WO | 2008/107918 A1 | 9/2008 |

OTHER PUBLICATIONS

European Examination Report dated Apr. 17, 2018, in EP Appln. No. 16 167 444.

* cited by examiner

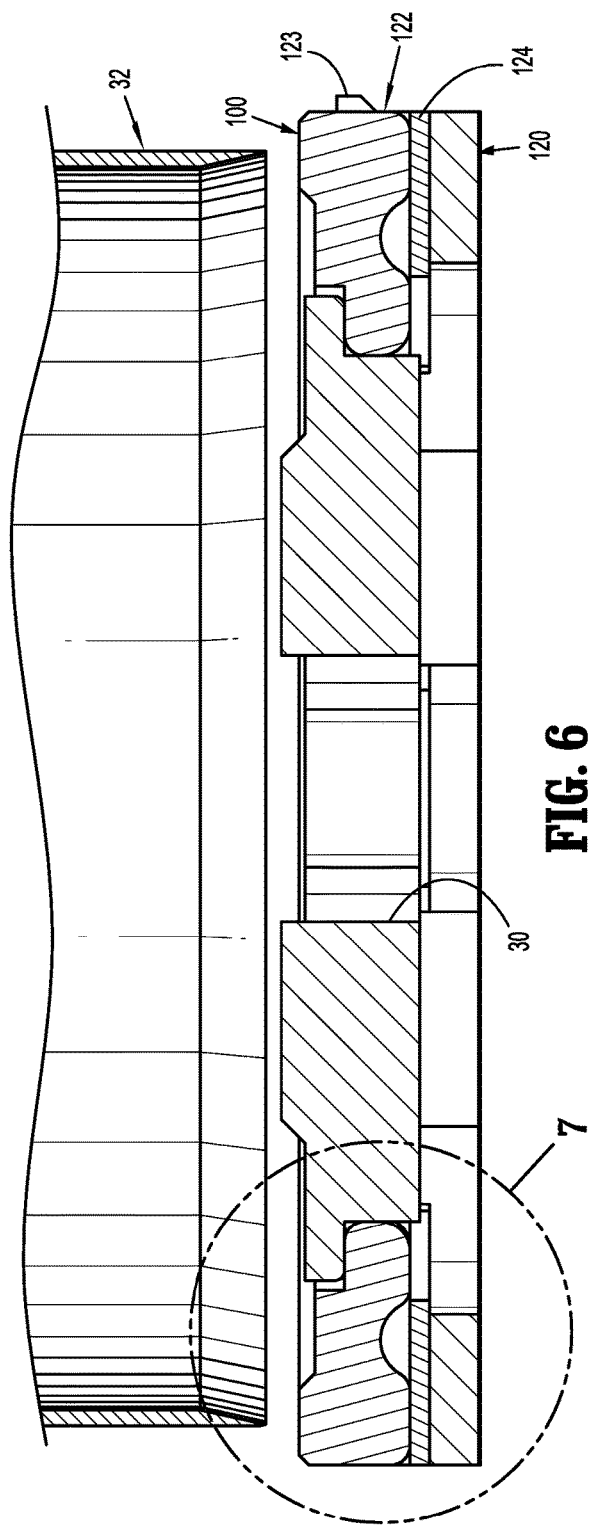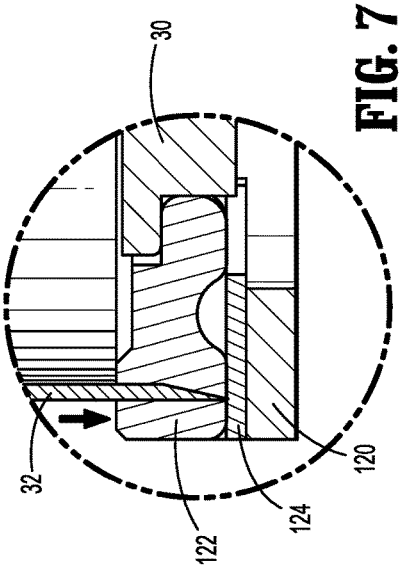

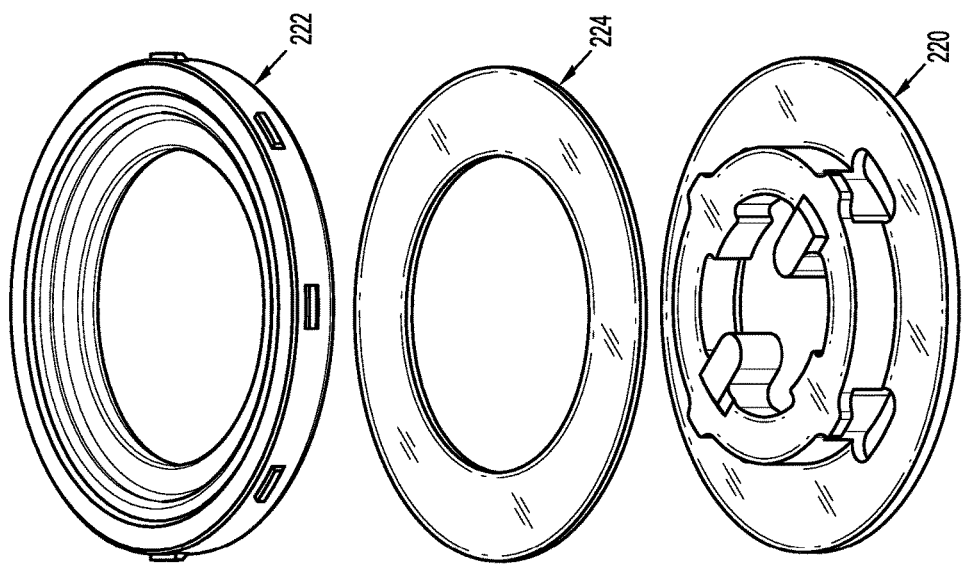
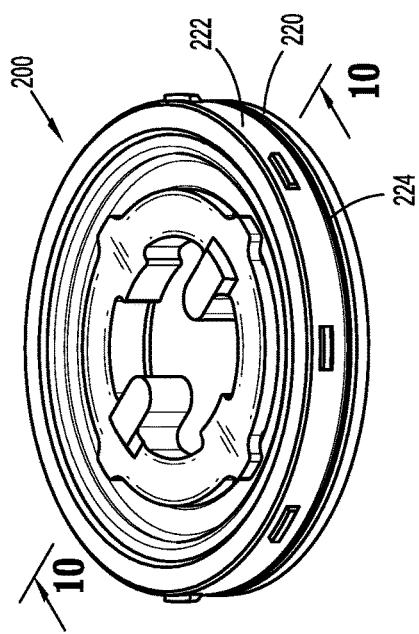
FIG. 8
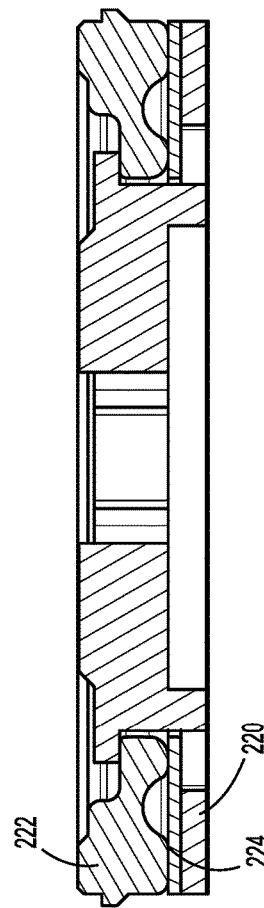
FIG. 9
FIG. 10

CUTTING RING ASSEMBLY WITH RIGID CUTTING MEMBER

CROSS-REFERENCE TO RELATED APPLICATIONS

This application claims the benefit of and priority to U.S. Provisional Patent Application No. 62/154,213, filed Apr. 29, 2015, the entire disclosure of which is incorporated by reference herein.

BACKGROUND

1. Technical Field

The present disclosure relates to a cutting ring assembly for use with a surgical stapling device. More specifically, the present disclosure relates to a cutting ring assembly for use with a circular stapling device having a thin, rigid cutting member.

2. Background of Related Art

Surgical stapling devices having an end effector configured to clamp and suture tissue are well known in the medical arts. Typically, these devices include a first jaw that supports an anvil assembly and a second jaw that supports a cartridge assembly which houses a plurality of staples. The first and second jaws are movable in relation to each other between spaced and approximated positions to clamp tissue between the jaws prior to firing the staples into the tissue. The first and second jaws may also support two part fasteners or first and second compression members that interact to suture tissue.

Circular stapling devices are used to perform end-to-end anastomosis procedures within a patient. During an end-to-end anastomosis procedure, an end of a first vessel portion is joined to an end of a second vessel portion. It is not uncommon in such procedures for the ends of the vessel portions to be joined to include staple lines that seal the end of each of the vessel portions.

Typically, circular stapling devices include an annular knife which translates through the anvil and cartridge assemblies to core tissue within the first and second vessel portions to provide an unobstructed passage within the joined vessel portions. It is common for the anvil assembly to include a backup member, e.g., a cutting washer, positioned to engage the annular knife to allow the knife to more easily cut through tissue. However, even with the inclusion of a backup member, the annular knife of conventional circular stapling devices may have difficulty cutting through staples or sutures positioned in tissue between the annular knife and the cutting washer.

A need exists in the medical arts for an improved backup member for use with a circular stapling device that allows for effective coring of tissue and sutures positioned in tissue.

SUMMARY

One aspect of the present disclosure is directed to an anvil assembly including an anvil center rod, an anvil head supporting an anvil plate having a plurality of staple deforming pockets, and a cut ring assembly supported within the anvil head adjacent the anvil plate. The cut ring assembly includes a backup member, an intermediate member and a cutting ring body. The intermediate member is formed of a thin, rigid material and is sandwiched between the backup member and the cutting ring body. The thin, rigid material is formed of a material having a hardness less than the hardness of the backup member and greater than the hardness of the cutting ring body.

In embodiments, the intermediate member has a thickness of between 0.005 inch and 0.020 inch. In certain embodiments, the intermediate member has a thickness of 0.010 inch.

In some embodiments, the intermediate member is secured to the backup member with an adhesive and the cutting ring body is secured to the intermediate member with an adhesive.

In some embodiments, the cutting ring body is molded onto the backup member and the intermediate member.

In certain embodiments, the backup member is formed from a metal, the cutting ring body is formed of a plastomer and the intermediate member is formed of a rigid plastic material. The backup member can be formed from stainless steel and the intermediate member can be formed from a polymer such as a polyester, e.g., polyethylene terephthalate (PET or PETG).

In embodiments, the anvil head defines an anvil post and each of the backup member, the cutting ring body, and the intermediate member defines a central opening. The cutting ring assembly is slidable about the post of the anvil head.

In embodiments, the backup member defines a platform which is received within the openings of the cutting ring body and the intermediate member.

In some embodiments, the backup member forms an inner surface of the anvil head.

In another aspect of the disclosure a cut ring assembly includes a backup member, an intermediate member and a cutting ring body. The intermediate member is sandwiched between the backup member and the cutting ring body and is formed of a thin, rigid material having a hardness less than the hardness of the backup member and greater than the hardness of the cutting ring body.

In embodiments, the intermediate member has a thickness of between 0.005 inch and 0.020 inch. In certain embodiments, the intermediate member has a thickness of 0.010 inch.

In some embodiments, the intermediate member is secured to the backup member with an adhesive and the cutting ring body is secured to the intermediate member with an adhesive.

In certain, embodiments, the cutting ring body is molded onto the backup member and the intermediate member.

In some embodiments, the backup member is formed from a metal, the cutting ring body is formed of a plastomer and the intermediate member is formed of a rigid plastic material.

In embodiments, the backup member is formed from stainless steel and the intermediate member is formed from a polymer such as a polyester, e.g., polyethylene terephthalate (PET or PETG).

In embodiments, the backup member defines a platform which is received within the openings of the cutting ring body and the intermediate member.

BRIEF DESCRIPTION OF THE DRAWINGS

Various embodiments of the presently disclosed cutting ring assembly are described herein with reference to the drawings, wherein:

FIG. 6 is a cross-sectional view taken along section lines 6-6 of FIG. 4;

FIG. 7 is an enlarged view of the indicated area of detail shown in FIG. 6;

FIG. 8 is a side perspective view of another embodiment of the presently disclosed cutting ring assembly;

FIG. 9 is a side perspective view of the cutting ring assembly shown in FIG. 8 with parts separated; and FIG. 10 is a cross-sectional view of the cutting ring assembly taken along section line 10-10 of FIG. 8.

DETAILED DESCRIPTION OF EMBODIMENTS

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the described embodiments. Accordingly, the disclosure is not to be limited by what has been particularly shown and described, except as indicated by the appended claims.

As used herein, the term distal refers to that portion of the device which is farthest from the clinician, while the term proximal refers to that portion of the instrument which is closest to the clinician. In addition, as used herein, the term clinician refers to medical staff including doctors, nurses and support personnel.

The present disclosure is directed to a cutting ring assembly, described in detail below, which includes a thin, rigid member positioned between a hard back up member and a softer cutting member. The thin rigid member provides a shearing surface that facilitates cutting through hard staples which may be positioned in tissue being sutured. The thin rigid member also allows a knife blade which may be deformed as the knife blade engages a hard staple to pass cleanly through the staple. Additional advantages of the presently disclosed cutting ring assembly are described below.

Figure 1:
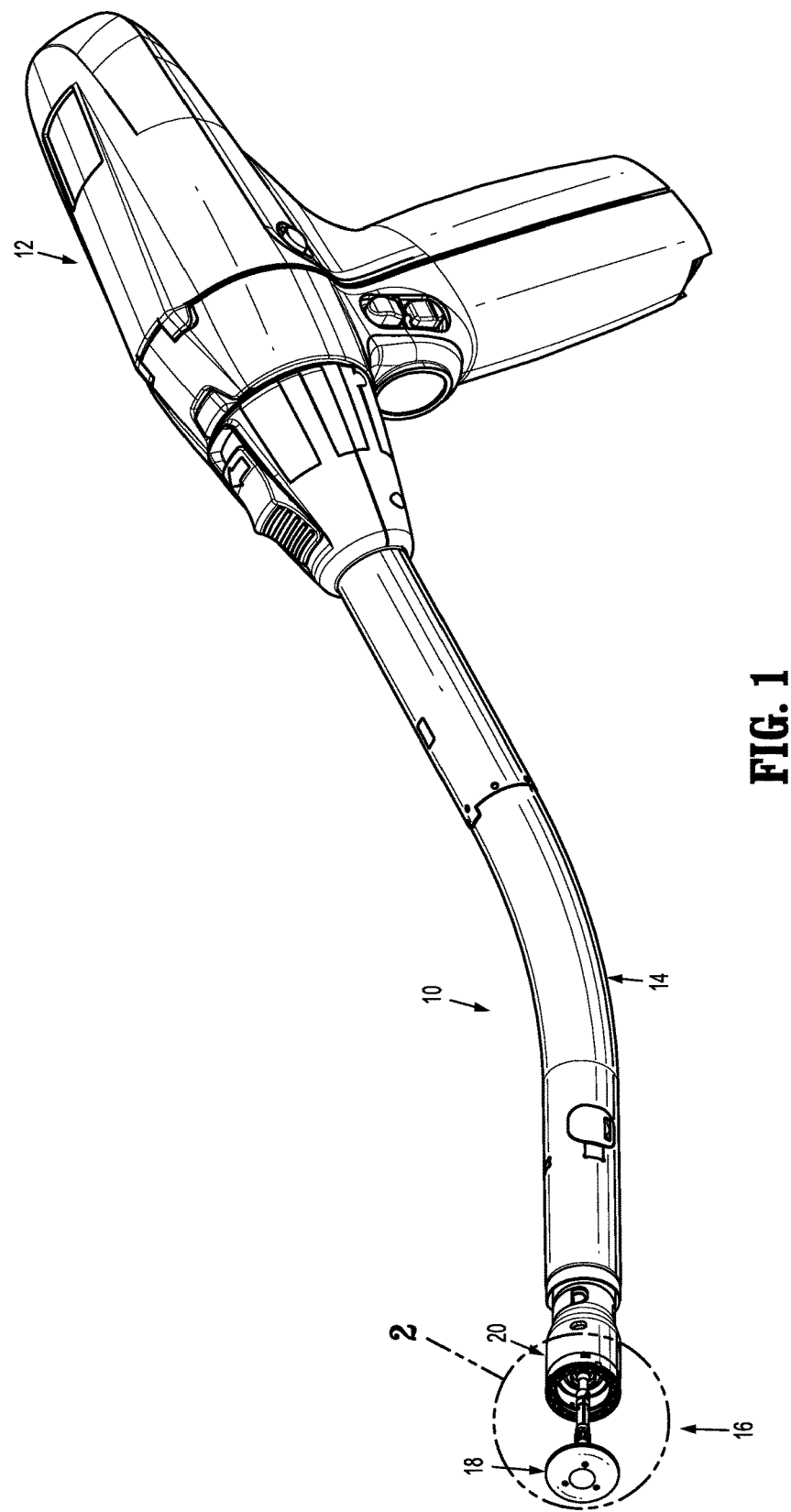
FIG. 1 is a side perspective view of a surgical stapling device including an end effector in an unapproximated position.
Figure 2:
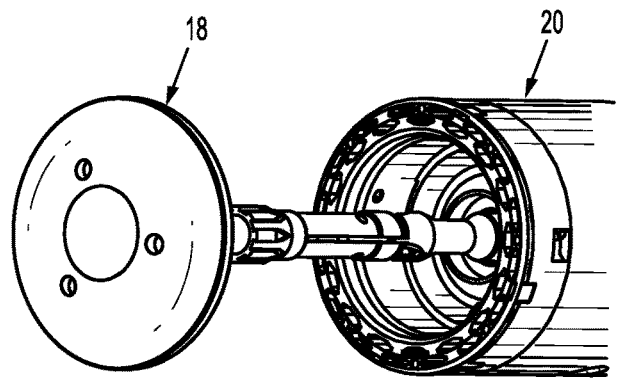
FIG. 2 is an enlarged view of the indicated area of detail shown in FIG. 1.

FIGS. 1 and 2 illustrate a surgical stapling device 10 including a handle assembly 12, an elongated body portion 14 which is supported by and extends distally from the handle assembly 12, and an end effector 16 supported on a distal end of the elongated body portion 14. Although the handle assembly 12 is illustrated as including an electromechanical hand piece, it is envisioned that the presently disclosed cutting ring assembly discussed in further detail below is suitable for use with stapling devices having manually actuated handpieces such as disclosed in U.S. Pat. No. 7,303,106 ("the '106 patent") which is incorporated herein by reference in its entirety. The end effector 16 includes an anvil assembly 18 and a shell or cartridge assembly 20.

Figure 3:
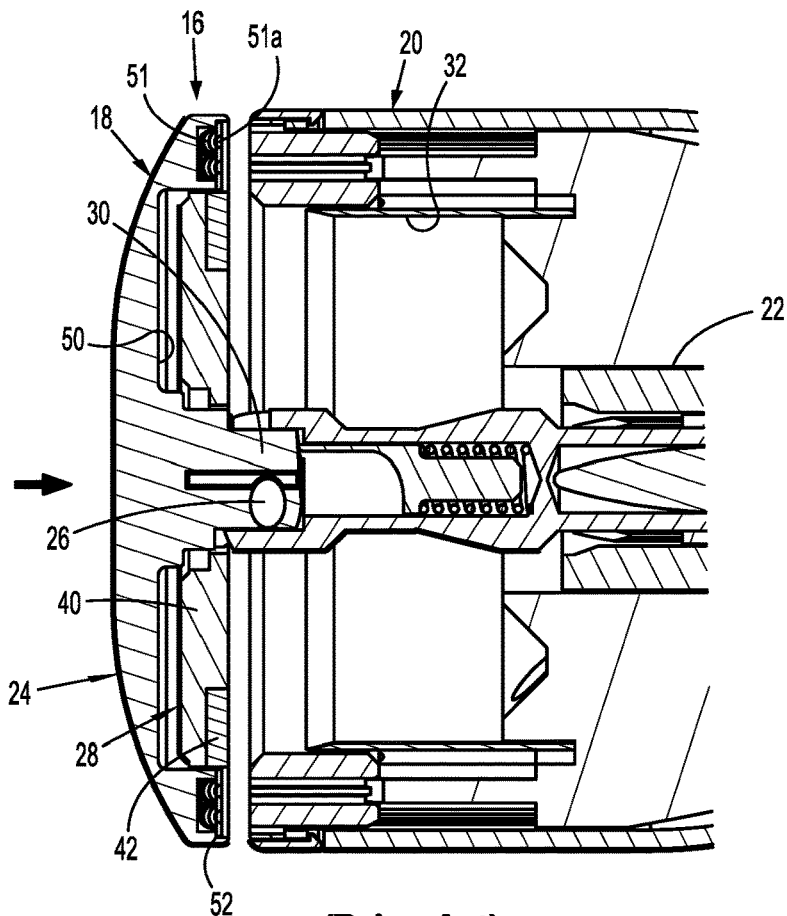
FIG. 3 is a side cross-sectional view through the end effector of a conventional surgical stapler.

FIG. 3 illustrates a conventional anvil assembly 18 that includes, inter alia, an anvil center rod 22, a pivotal anvil head 24 supported on the anvil center rod 22 about a pivot member 26, and a cutting ring assembly 28 that is slidable about a post 30 of the anvil head 24. The cutting ring assembly 28 is axially aligned with and positioned to engage an annular knife 32 of the cartridge assembly 20. U.S. Pat. No. 7,494,038 ("the '038 patent") discloses an anvil assembly similar to that shown in FIG. 3 and is incorporated herein by reference in its entirety.

As best shown in FIG. 3, the cutting ring assembly 28 of the anvil assembly 18 includes a backup plate 40 and a cutting ring body 42 that is positioned on the backup plate 40. The backup plate 40 is formed from a hard material such as a metal, e.g., sintered stainless steel, and the cutting ring body 42 is formed of a softer material such as polyethylene or a plastomer, e.g., metallocene.

Figure 4:
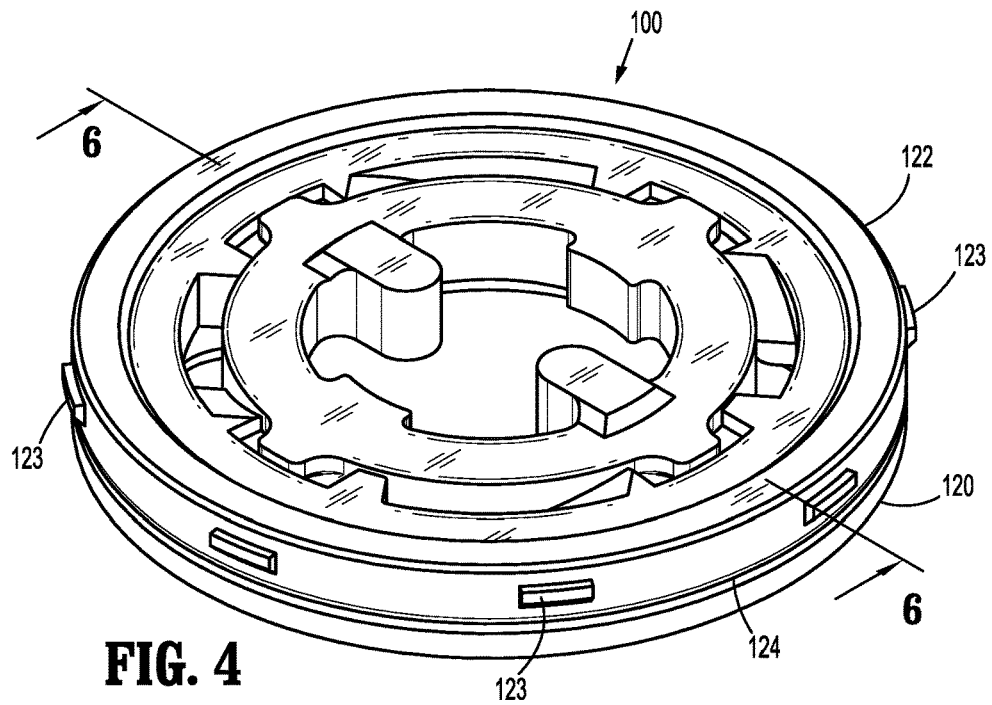
FIG. 4 is a side perspective view of one embodiment of the presently disclosed cutting ring assembly.
Figure 5:
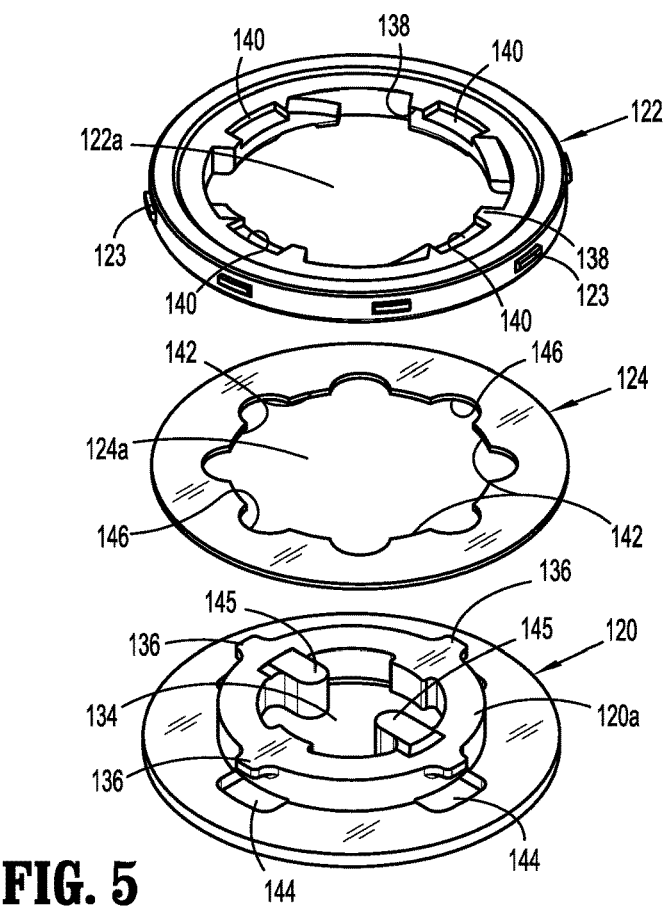
FIG. 5 is a side perspective view of the cutting ring assembly shown in FIG. 4 with parts separated.

FIGS. 4 and 5 illustrate one embodiment of the presently disclosed cutting ring assembly shown generally as 100. The cutting ring assembly 100 is suitable for use in the anvil head 24. Thus, the components of the anvil head 24, excluding the cutting ring assembly 100, will be described with reference to FIG. 3. Cutting ring assembly 100 includes a backup member 120, a cutting ring body 122 and an intermediate member 124. The backup member 120 includes a substantially centrally located opening 134 which is dimensioned to be positioned about the post 30 (FIG. 3) of the anvil head 24 within an inner annular recess 50 of the anvil head 24. The inner annular recess 50 of the anvil head 24 is located between the post 30 and an outer annular recess 52 which receives an anvil plate 51 having a plurality of staple forming depressions 51a.

Backup member 120 includes a raised center platform 120a. The cutting ring body 122 defines an opening 122a that has an inner configuration substantially the same as the platform 120a such that the cutting ring body 122 is received about the platform 120a. A pair of diametrically opposed fingers 123 extend inwardly from the platform 120a and function to prevent the anvil head 24 (FIG. 1) from tilting prior to firing of the stapling device 10 such as taught in '038 patent which is incorporated herein by reference as discussed above.

The intermediate member 124 also defines an opening 124a that is configured to receive the post 30 of the anvil head 24. The intermediate member 124 is sandwiched between the backup member 120 and the cutting ring body 122. The backup member 120, cutting ring body 122 and the intermediate member 124 can be fixedly secured together using adhesives. Alternately, the cutting ring body 122 can be molded about the backup member 120 and the intermediate member 120 after the intermediate member 124 is assembled onto the backup member 120.

In embodiments, the backup member 120 includes a plurality of radially extending tabs 136 that extend outwardly from the raised platform 120a and the cutting ring body 122 includes a series of tabs 138 and recesses 140 defined along an inner periphery of the cutting ring body 122 about the opening 122a. The tabs 136 are received within the recesses 140 and the tabs 138 engage an outer periphery of the raised platform 120a to properly position the cutting ring body 122 about the raised platform 120a. Similarly, the intermediate member 124 includes a series of inwardly extending tabs 142 formed about the opening 124a which engage the outer periphery of the raised platform 120a to properly position the intermediate member 124 about the raised platform 120a.

As shown in FIG. 5, the backup member 120 also defines openings 144 and the intermediate member 124 defines scallops 146. When the cutting ring assembly 100 is assembled, the openings 144 in the backup member 120, the scallops 146 in the intermediate member 124 and the recesses 140 in the cutting ring body 122 communicate with each other to allow fluid to pass through the cutting ring assembly 100.

In embodiments, the cutting ring assembly 100 is configured to be slidable about the post 30 of the anvil head 24. In such embodiments, the backup member 120 can include a pair of inwardly extending fingers 145 which are configured to engage a surface of the anvil center rod 22 (FIG. 3) to prevent the anvil head 24 from tilting in relation to the anvil center rod 22. This tilting operation is described in detail in the '038 patent which has been incorporated by reference into this application as discussed above. As such, no further discussion of the operation of the tilting anvil head 24 is included in this application.

The outer surface of the cutting ring body 122 may include a series of outwardly extending projections 123 which are positioned to be received within recesses or an annular recess (not shown) within the anvil head 24 to secure the cutting ring body 122 within the anvil head 124. Alternately, other fastening techniques can be used to secure the cutting ring body 122 within the anvil head 24.

As discussed above with regard to the cutting ring assembly 28, the backup member 120 of the cutting ring assembly 100 is formed of a hard material such as a metal, e.g., sintered stainless steel, and the cutting ring body 122 is formed of a softer material, e.g., a plastomer or polyethylene. The intermediate member 124 is formed of a material that is harder than the cutting ring body 122 but softer than the backup member 120. In one embodiment, the intermediate member 124 is formed of a thin, rigid plastic material. For example, the intermediate member can be formed of a polymer, such as a polyester, e.g., a polyethylene terephthalate (PET or PETG). In embodiments, the intermediate member 124 is sandwiched between the backup member 120 and the cutting ring body 122 and has a thickness of from about 0.005 of an inch to about 0.020 of an inch. In other embodiments, the cutting ring body 122 has a thickness of about 0.010 of an inch.

Although the cutting ring assembly 100 is disclosed as being slidably positioned about the post 30 of the anvil head 24, it envisioned that the cutting ring assembly 100 can be securely fastened within the anvil head 24 and that the backup member 120 can be defined by or form an inner surface of the anvil head 24. More specifically, the backup member 120 can be integrally formed with the inner surface of the anvil head 24 (FIG. 3). In such an embodiment, the intermediate member 124 is secured directly to the inner surface of the anvil head 24 and the cutting ring body 122 is secured to an upper surface of the intermediate member 124.

Referring to FIGS. 6 and 7, when the stapling device 10 (FIG. 1) is actuated to advance the annular knife 32 towards the cutting ring assembly 100, the annular knife 32 travels through the softer material of the cutting ring body 122, into the harder surface of the intermediate member 124, and into the harder surface of the backup member 120. As discussed above, the backup member 120 may be movably supported about the post 30 of the anvil head 24 or define a inner wall of the anvil head 24.

The provision of an intermediate member 124 as described above between the backup member 120 and the cutting ring body 122 provides a number of advantages over conventional cutting ring assemblies in addition to those discussed above. For example, the thin, hard surface of the intermediate member 124 provides a shearing surface for cutting through harder staples that may get embedded in the softer cutting ring body. The use of a thin, hard surface may also reduce the cutting forces required to cut tissue as compared to cutting tissue against a metal surface. The provision of a thin, rigid material also enables the use of less expensive metal materials which have rough surface finishes to form the backup member (or inner surface of the anvil head) against which the annular knife bottoms out and the flatness tolerance of the metal surface below the cutting ring body to be less tight since the thickness of the thin, rigid material will compensate for the imperfections in the metal surface.

FIGS. 8-10 illustrate an alternate embodiment of the presently disclosed cutting ring assembly shown generally as 200. Cutting ring assembly 200 is substantially similar to cutting ring assembly 100 and includes a backup member 220, a cutting ring body 222 and an intermediate member 224. The backup member 220 is identical to the backup member 120 and will not be discussed in further detail herein. The cutting ring member 222 is similar to cutting ring member 122 except that the opening 222a is circular and does not include the series of tabs 138 and recesses 140 that are provided along the inner periphery of the cutting ring body 122 of cutting ring assembly 100. Similarly, the intermediate member 224 is similar to the intermediate member 124 except that the inner periphery of the intermediate member 224 is circular and does not include the tabs 142 and scallops 146 of the intermediate member 124. The cutting ring assembly 200 functions in a substantially similar manner to the cutting ring assembly 100 and will not be described in further detail herein.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An anvil assembly comprising:
   an anvil center rod;
   an anvil head supporting an anvil plate having a plurality of staple deforming pockets; and
   a cut ring assembly supported within the anvil head adjacent the anvil plate, the cut ring assembly including a backup member, an intermediate member and a cutting ring body, the backup member formed of a single integral material, wherein the intermediate member is formed of a thin, rigid material and is sandwiched directly between the backup member and the cutting ring body, wherein the intermediate member is in direct contact with the backup member and the cutting ring body, the thin, rigid material being formed of a material having a hardness less than the hardness of the backup member and greater than the hardness of the cutting ring body.

2. The anvil assembly according to claim 1, wherein the intermediate member has a thickness of between 0.005 of an inch and 0.020 of an inch.

3. The anvil assembly according to claim 1, wherein the intermediate member has a thickness of 0.010 of an inch.

4. The anvil assembly according to claim 1, wherein the intermediate member is secured to the backup member with an adhesive.

5. The anvil assembly according to claim 4, wherein the cutting ring body is secured to the intermediate member with an adhesive.

6. The anvil assembly according to claim 1, wherein the cutting ring body is molded onto the backup member and the intermediate member.

7. The anvil assembly according to claim 1, wherein the backup member is formed from a metal, the cutting ring body is formed of a plastomer and the intermediate member is formed of a rigid plastic material.

8. The anvil assembly according to claim 7, wherein the backup member is formed from stainless steel and the intermediate member is formed from a polymer.

9. The anvil assembly according to claim 1, wherein the anvil head defines an anvil post and each of the backup member, the cutting ring body, and the intermediate member defines a central opening, the cutting ring assembly being slidably positioned about the post of the anvil head.

10. The anvil assembly according to claim 9, wherein the backup member defines platform which is received within the openings of the cutting ring body and the intermediate member.

11. The anvil assembly according to claim 1, wherein the backup member forms an inner surface of the anvil head.

12. A cut ring assembly comprising:
a backup member, an intermediate member and a cutting ring body, the intermediate member being sandwiched directly between the backup member and the cutting ring body and being formed of a thin, rigid material having a hardness less than the hardness of the backup member and greater than the hardness of the cutting ring body, the backup member formed of a single integral material.

13. The anvil assembly according to claim 12, wherein the intermediate member has a thickness of between 0.005 inch and 0.020 inch.

14. The anvil assembly according to claim 13, wherein the intermediate member has a thickness of 0.010 inch.

15. The anvil assembly according to claim 12, wherein the intermediate member is secured to the backup member with an adhesive.

16. The anvil assembly according to claim 12, wherein the cutting ring body is secured to the intermediate member with an adhesive.

17. The anvil assembly according to claim 12, wherein the cutting ring body is molded onto the backup member and the intermediate member.

18. The anvil assembly according to claim 12, wherein the backup member is formed from a metal, the cutting ring body is formed of a plastomer and the intermediate member is formed of a rigid plastic material.

19. The anvil assembly according to claim 18, wherein the backup member is formed from stainless steel and the intermediate member is formed from a polymer.

20. The anvil assembly according to claim 12, wherein the backup member defines platform which is received within the openings of the cutting ring body and the intermediate member.

* * * * *